United States Patent [19]

Dolhyj et al.

[11] 4,218,572

[45] Aug. 19, 1980

[54] PROCESS FOR THE PRODUCTION OF POLYPHENYLS

[75] Inventors: Serge R. Dolhyj, Parma; Louis J. Velenyi, Lyndhurst, both of Ohio

[73] Assignee: Standard Oil Company, Cleveland, Ohio

[21] Appl. No.: 946,696

[22] Filed: Sep. 28, 1978

[51] Int. Cl.$^2$ ............... C07C 5/38; C07C 15/14; B01J 23/22

[52] U.S. Cl. ............... 585/400; 252/456; 252/464; 562/461; 562/470; 585/262; 585/427

[58] Field of Search ............... 260/668 D; 562/461, 562/470; 252/456, 464; 585/400, 433, 434

[56] References Cited

U.S. PATENT DOCUMENTS

| | | | |
|---|---|---|---|
| 2,742,515 | 4/1956 | Stuart | 260/668 D |
| 3,928,481 | 12/1975 | Suggitt | 260/668 D |
| 3,928,484 | 12/1975 | Suggitt | 260/668 D |
| 3,962,362 | 6/1976 | Suggitt | 260/668 R |
| 4,123,470 | 10/1978 | Murtha | 260/668 D |
| 4,152,300 | 5/1979 | Riesser | 252/464 X |

*Primary Examiner*—Delbert E. Gantz
*Assistant Examiner*—G. E. Schmitkons
*Attorney, Agent, or Firm*—Gary R. Plotecher; Herbert D. Knudsen; Larry W. Evans

[57] ABSTRACT

Substituted or unsubstituted cyclohexylbenzene is dehydrogenated to substituted or unsubstituted biphenyl in the absence of oxygen over an oxide complex catalyst. The oxide complex catalyst comprises at least one element selected from the group consisting of Group VB and Group VIII elements, optionally promoted with at least one element selected from the group consisting of Group IA, Group IB, Group IIB, Group VIIB and Group VIB.

21 Claims, No Drawings

PROCESS FOR THE PRODUCTION OF POLYPHENYLS

BACKGROUND OF THE INVENTION

The present invention relates to a novel process for making substituted or unsubstituted polyphenyls. More particularly, this invention relates to the dehydrogenation of cyclohexylbenzene to biphenyl.

There are many known methods for manufacturing polyphenyls. Among these methods is the thermal dehydrogenation of benzene and the partial oxidation of benzene. However, it is well known to those skilled in the art that higher molecular weight aromatics, typified by biphenyls and terphenyls, may be difficult to prepare in high purity because of their high boiling points which preclude distillation at reasonable temperatures and pressures. Furthermore, it may be difficult to attain these materials in high purity because many techniques by which they may be recovered give undesirable yields of byproducts or require very severe processing conditions. Thus, it is very important to develop a process for producing polyphenyls which is very selective with high conversions.

The present invention relates to a novel process for producing substituted and unsubstituted polyphenyls from the corresponding substituted and unsubstituted cyclohexylbenzenes. This process can be carried out in a simple and straightforward manner to yield the desired end products with extremely high selectivities and conversions. In fact, by using the process disclosed in the instant invention, selectivities approaching 100% are obtained.

SUMMARY OF THE INVENTION

It has now been discovered that biphenyl can be produced by dehydrogenating cyclohexylbenzene in the absence of oxygen over a catalyst comprising an oxide complex of at least one metal from the group consisting of Group VB and Group VIII of the Periodic Table. It has also been found that substituted cyclohexylbenzene can be converted to the corresponding substituted biphenyl.

Thus, the present invention provides a novel process for the catalytic dehydrogenation of cyclohexylbenzene or substituted cyclohexylbenzene to biphenyl or substituted biphenyl by contacting the cyclohexylbenzene or substituted cyclohexylbenzene with a catalyst comprising a Group VB or Group VIII metal oxide or oxide complex. More specifically, the present invention provides a process for the catalytic dehydrogenation of cyclohexylbenzene to biphenyl in which the cyclohexylbenzene is contacted with a catalyst of the formula:

$$A_a B_b O_x$$

wherein
A is one or more elements selected from the group consisting of Group VB and Group VIII metals or mixtures thereof;
B is one or more elements selected from the group consisting of Group IA, Group IB, Group IIB, Group VIIB and Group VIB or mixtures thereof; and wherein
a is 0.1 to 10;
b is 0 to 10; and
x is the number of oxygens required to satisfy the valence requirements of the other elements present.

In a specific embodiment, the present invention also provides a process for the vapor phase catalytic dehydrogenation of cyclohexylbenzene to biphenyl in which the cyclohexylbenzene is contacted with a catalyst containing vanadium.

Finally, the instant invention also provides a process for the partial dehydrogenation of substituted or unsubstituted cyclohexylbenzene to substituted or unsubstituted phenylcyclohexene.

DETAILED DESCRIPTION

Reactants

The reactants in the present invention are substituted or unsubstituted cyclohexylbenzene having the structure:

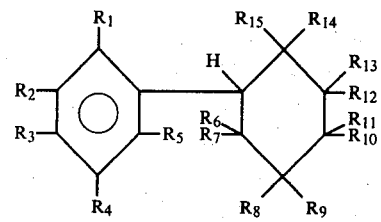

wherein $R_1$ thru $R_{15}$ are each independently selected from:
(1) hydrogen;
(2) methyl;
(3) unsubstituted phenyl;
(4) substituted phenyl substituted with one to five methyl groups;
(5) —$CH_2$—O—$CH_3$ and
(6) —$CH_2$—COO—$CH_3$.

Preferred reactants are wherein $R_1$ thru $R_{15}$ are each independently selected from hydrogen and methyl. The most preferred reactant is cyclohexylbenzene and substituted cyclohexylbenzene substituted with 1 to 2 methyl groups.

Any material which is inert to the reactants, catalysts and products of the inventive reaction can also be included in the reaction system as a diluent. For example, steam, nitrogen gas, inert gases and carbon dioxide could be added to the reaction system, if desired.

Process Conditions

In carrying out the inventive process, the cyclohexylbenzene or substituted cyclohexylbenzene is contacted with a catalyst as described below for effecting the dehydrogenation process. The inventive reaction can be accomplished both in a batch mode and continuously with both fixed and fluid catalyst beds. The instant reaction can also take place in either the gas phase or liquid phase.

Reaction temperatures are normally maintained between 300° to 700° C. and more preferably 450° to 600° C. The reaction pressure is normally maintained at atmospheric pressure but it may also be conducted at subatmospheric or superatmospheric pressure. The apparent contact time of the catalyst and the reactants may vary from about 0.1 to 20 seconds for the fixed-bed process, preferably 1 to 10 seconds and more preferably about 3 seconds. A corresponding contact time is used for fluid bed processes. In general, lower reaction temperatures rquire longer contact times and higher reaction temperatures require shorter contact times.

Catalysts

The catalysts employed in the inventive process comprise oxides or oxide complexes. These catalysts can be described by the formula:

$$A_a B_b O_x$$

wherein
A is at least one element selected from the group consisting of Group VB and Group VIII metals or mixtures thereof;
B is at least one element selected from the group consisting of Group IA, Group IB, Group IIB, Group VIIB and Group VIB or mixtures thereof; and wherein
a is about 0.1 to 10;
b is about 0 to 10; and
x is the number of oxygens sufficient to satisfy the valence requirements of the other elements present.

The catalyst may be any catalyst delineated by the general formula above with respect to the components of the catalyst. Preferred catalysts contain at least one element selected from the group consisting of vanadium, iron, cobalt and nickel. Most preferably, these catalysts also contain at least one element selected from the group consisting of chromium, molybdenum, tungsten, zinc, potassium, manganese, silver and copper.

The exact chemical nature of the catalyst of the invention is not known. The catalyst may be a mixture of oxides, for example, or an oxide complex of all the contained elements. In any event, these types of catalysts are generally known in the art.

The catalysts of the invention can be made by techniques which are essentially the same as those techniques described in the art for other catalysts. (See U.S. Pat. No. 3,642,930, which is herein incorporated by reference). Even though there are numerous preparations which may be utilized to give acceptable catalysts, some of the preferred methods of making the catalysts are described below.

The catalysts of the present invention can be prepared from any mixture of compounds that can be calcined to give the desired oxide component. Preferably, the catalysts are prepared by coprecipitating decomposable salts such as nitrates, acetates, halides and/or oxides to form a catalyst precursor, and then calcining the precursor in the presence of oxygen. Other known catalyst preparation techniques, however, can be employed.

The catalytic activity embodied in the present invention is enhanced by heating the catalysts at elevated temperatures. Preferably, the catalysts are dried and heated at a temperature of about 260° C. to 1,000° C., more preberably at about 425° C. to 700° C., for from 2 to 24 hours. If the activity/selectivity relationship is not satisfactory, the catalysts can be further heat treated at a temperature above about 425° C. but below a temperature deleterious to the catalyst, preferably in the range from about 425° C. to about 800° C. for from 1 to 48 hours.

The catalyst, if desired, can be supported on a suitable support. Preferred support materials are $SiO_2$, $Al_2O_3$, SiC, carbon, $TiO_2$, and rare earth exchanged Y-type zeolites. Any other known support material can be used which is stable under the reaction conditions to be encountered in the use of the catalyst.

Recovery

The reaction product obtained upon completion of the reaction is normally in the form of a gas and composed primarily of cyclohexylbenzene or substituted cyclohexylbenzene, phenylcyclohexene and substituted or unsubstituted biphenyl. This reaction product can be subjected to suitable known separation techniques to yield the desired end product, namely the biphenyl or substituted biphenyl.

For example, the product gas can be condensed and the reaction product separated from any carrier gas that may be in the system. The liquid reaction product can then be filtered to remove catalyst therefrom and then separated into component parts by the use of an acetone trap and distillation or by any other suitable separation techniques.

As is well known, biphenyl and other polyphenyls serve mainly as heat transfer fluids. Biphenyls have also been used as a paper impregnant for citrus fruit wrappers and as a dye carrier, particularly for plastics and for synthetic fibers. The chlorinated biphenyls are probably the most important commercial derivatives. 4-hydroxylbiphenyl reacts with formaldehyde to give a resin used in wear resistant surface coatings. 2-hydroxybiphenyl, particularly as its sodium salt, is used as a preservative, germacide or fungicide. The 4,4-diaminobiphenyl is an important dye intermediate. Biphenyls may also be alkylated and sulfonated to produce wetting agents.

SPECIFIC EMBODIMENTS

In order to more thoroughly describe the present invention, the following working examples are presented. In each of these examples, cyclohexylbenzene is dehydrogenated in a 40 cc fixed-bed reactor. The gaseous feed is introduced via a calibrated rotometer and the liquid feed is supplied directly into the reactor using a Sage syringe pump. The reactor is heated in a stainless steel block to the desired reaction temperature.

In general, the experimental method consists of dehydrogenating the liquid reactant in the absence of oxygen by contacting it with a catalyst to produce biphenyl. The reactions are run at 350° C. to 620° C. at one atmospheric total pressure. Standard run conditions in all examples, unless otherwise indicated, comprise a hydrocarbon/$N_2$/$H_2O$ ratio of 1/10/10 and a contact time of 3 seconds.

In all runs, the offgas is collected at the reactor exit. The biphenyl is scrubbed in an acetone trap. The liquid products are quantitatively analyzed using an HP chromatograph.

For the purposes of this application, the following definitions are used:

$$\% \text{ Conv.} = \frac{\text{Gms. carbon cyclohexylbenzene reacted}}{\text{Gms. carbon cyclohexylbenzene fed}} \times 100$$

$$\% \text{ Yield} = \frac{\text{Gms. carbon cyclohexylbenzene conv. to prod.}}{\text{Gms. carbon cyclohexylbenzene fed}} \times 100$$

The results have all been adjusted to a 100% carbon balance.

The following experiments were conducted:

EXAMPLES 1 AND 2

72 gms. of $MoO_3$, 11.36 gms. of $V_2O_5$, 20.42 gms. of $Mn(CH_3CO_2)_2.4H_2O$ and 9.19 gms. of W powder were dissolved in 600 cc. of distilled $H_2O$. The resultant slurry (Solution A) was refluxed for 2 hours. In a separate beaker, 16.64 gms. of $Cu(CH_3CO_2)_2.H_2O$ and 6.95 gms. of $Ag(CH_3CO_2)$ were dissolved in 300 cc. of distilled water. This solution (Solution B) was added to Solution A and refluxed for 1 hour. Then, 50.4 gms. of 41% Silica Sol and 6.89 gms. of a rare earth exchanged Y-type zeolite designated Linde's SK-500 (<50 mesh) were added. This mixture was evaporated to a thick black paste and dried over a weekend at 110° C. The resultant black brittle material comprised 80% $(Mo_{12}V_3W_{1.2}Cu_2Mn_2AgO_x)$ 15% $SiO_2$ 5% SK-500.

The catalyst so obtained was charged into a 40 cc. fixed bed reactor. One mole of cyclohexylbenzene, 10 moles of nitrogen gas and 10 moles of water were fed into the reactor. The temperature was varied from 350° C. to 400° C. for examples 1 and 2 and the results are shown in Table 1.

EXAMPLES 3 TO 5

42.8 gms. of $Al_2O_3$ was dispersed in 1 liter of distilled $H_2O$ containing 8 gms. of 38% HCl, 40 gms. of $CrO_3$ crystals and 80 gms. of $KHCO_3$ were added to this solution. Finally, 71.96 gms. of $FeC_2O_4$ was slowly added. A violent gas evolution was observed and a precipitate formed. This precipitate was evaporated to a dark green paste and then dried overnight. The resultant hard, dark brown material was calcined for 2 hours at 550° C. The catalyst so obtained comprised 70% $K_2CrFeO_x.30\%$ $Al_2O_3$.

The catalyst obtained above was charged to a 40 cc. fixed-bed reactor. One mole of cyclohexylbenzene, 10 moles of nitrogen gas and 10 moles of water were added to this reactor. The reaction temperature varied from 450° C. to 550° C. in these three experiments. The results are shown in Table 1.

EXAMPLES 6 AND 7

22.5 gms. of $Al_2O_3$ were dispersed in 1 liter of distilled $H_2O$ containing 8 gms. of 38% HCl. To the opaque solution obtained, 46.8 gms. of $NH_4VO_3$ crystals and 43.95 gms. of $Zn(CH_3CO_2)_2.2H_2O$ were added. The resultant mixture was evaporated to a homogenous light orange paste and dried overnight at 110° C. The hard, light brown material obtained was then calcined for 2 hours at 550° C. The catalyst so obtained comprised 70% $V_2ZnO_x.30\%$ $Al_2O_3$.

The catalyst obtained above was charged with a 40 cc. fixed-bed reactor. One mole of cyclohexylbenzene, 10 moles of nitrogen gas and 10 moles of water were charged to this reactor. The reaction temperature varied from 500° C. to 550° C. for Examples 6 and 7 and the results are shown in Table 1.

EXAMPLES 8 TO 10

A C-64 Girdler catalyst comprising 2.5% $CrO_3.26\%$ $K_2Co_3.60\%$ $Fe_2O_3$ (dry basis) was charged into a 40 cc. reactor along with one mole of cyclohexylbenzene, 10 moles of nitrogen gas and 10 moles of water. The reaction temperature was varied from 350° C. to 550° C. and the results are shown in Table 1.

TABLE 1

DEHYDROGENATION OF CYCLOHEXYLBENZENE

| Example | Catalyst Type | Reaction Temp (°C.) | Ratio CXB/N₂/H₂O | % PPC CXB | % PPC Biphenyl | % PPC Ph-Cxene | % Selectivity (To Biphenyl) |
|---|---|---|---|---|---|---|---|
| 1 | 80% $(Mo_{12}V_3W_{1.2}Cu_2Mn_2AgO_x)$ 15% $SiO_2$ . 5% SK-500 | 350 | 1/10/10 | 89.4 | 10.6 | | 100.0 |
| 2 | 80% $(Mo_{12}V_3W_{1.2}Cu_2Mn_2AgO_x)$ 15% $SiO_2$ . 5% SK-500 | 400 | 1/10/10 | 65.3 | 34.7 | | 100.0 |
| 3 | 70% $(K_2CrFeO_x)$ 30% $Al_2O_3$ | 450 | 1/10/10 | 100.0 | TR | | 100.0 |
| 4 | " | 500 | 1/10/10 | 100.0 | TR | | 100.0 |
| 5 | " | 550 | 1/10/10 | 92.4 | 5.6 | 2.0 | 73.7 |
| 6 | 70% $(V_2ZnO_x)$ 30% $Al_2O_3$ | 500 | 1/10/10 | 6.0 | 94.0 | | 100.0 |
| 7 | " | 550 | 1/10/10 | 0.0 | 100.0 | | 100.0 |
| 8 | 2.5% $Cr_2O_3$ . 26% $K_2CO_3$ . 60% $Fe_2O_3$ (Dry basis) | 350 | 1/10/10 | 94.3 | 5.7 | | 100.0 |
| 9 | 2.5% $Cr_2O_3$ . 26% $K_2CO_3$ . 60% $Fe_2O_3$ (Dry basis) | 450 | 1/10/10 | 89.0 | 11.0 | | 100.0 |
| 10 | 2.5% $Cr_2O_3$ . 26% $K_2CO_3$ . 60% $Fe_2O_3$ (Dry basis) | 550 | 1/10/10 | 16.1 | 83.9 | | 100.0 |

Contact Time: 3 seconds
Pressure: 1 atmosphere

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims.

We claim:

1. A process for producing a polyphenyl by the catalytic dehydrogenation of substituted or unsubstituted cyclohexylbenzene comprising contacting said substituted or unsubstituted cyclohexylbenzene with a dehydrogenation catalyst having the following formula:

$$A_aB_bO_x$$

wherein
  A is either one or more elements selected from Group VB or one or more elements selected from Group VB and one or more elements selected from Group VIII;
  B is one or more elements selected from the group consisting of Group IA, Group IB, Group IIB, Group VIIB and Group VIB or mixtures thereof; and
wherein
  a is 0.1 to 10;
  b is 0 to 10; and
  x is the number of oxygens required to satisfy the valence requirements of the other elements present;

with the proviso that when the catalyst does not contain a Group VIII element then b must be greater than 0.

2. The process of claim 1 wherein said substituted or unsubstituted cyclohexylbenzene has the structure:

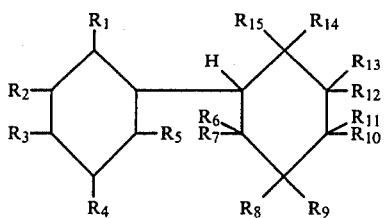

wherein $R_1$ thru $R_{15}$ are each independently selected from:
(1) hydrogen;
(2) methyl;
(3) unsubstituted phenyl;
(4) substituted phenyl substituted with one to four methyl groups;
(5) —$CH_2$—O—$CH_3$; and
(6) —$CH_2COOCH_3$.

3. The process of claim 2 wherein said $R_1$ thru $R_{15}$ are each independently selected from hydrogen and methyl.

4. The process of claim 3 wherein said $R_1$ thru $R_{15}$ are hydrogen.

5. The process of claim 1 wherein b is greater than zero.

6. The process of claim 1 wherein said catalyst contains at least one element selected from the group consisting of vanadium, iron, cobalt and nickel.

7. The process of claim 6 wherein said catalyst also contains at least one element selected from the group consisting of chromium, molybdenum, tungsten, potassium, manganese, zinc, and copper.

8. The process of claim 1 wherein said catalyst is supported on a support.

9. The process of claim 8 wherein said support is selected from the group consisting of $SiO_2$, $Al_2O_3$, SiC, C, $TiO_2$, and rare earth exchanged Y-type zeolites.

10. The process of claim 1 wherein said process is conducted at a temperature of 300° C. to 700° C.

11. The process of claim 10 wherein said process is conducted at a temperature of 450° C. to 600° C.

12. The process of claim 1 wherein said process is conducted in the absence of oxygen.

13. The process of claim 1 wherein the catalyst does not contain a nitrogeneous organic base.

14. The process of claim 1 wherein A is selected from the group consisting of Group VB elements or mixtures thereof.

15. The process of claim 14 wherein b is greater than 0.

16. The process of claim 15 wherein B is selected from the group consisting of Group IIB elements or mixtures thereof.

17. The process of claim 1 wherein said catalyst contains vanadium.

18. The process of claim 17 wherein said catalyst also contains zinc.

19. The process of claim 1 wherein B is selected from the group consisting of Group VIB elements.

20. The process of claim 1 wherein the catalyst contains at least one element from Group VB and at least one element from Group VIII metals.

21. The process of claim 20 wherein b is greater than 0.

* * * * *